(12) United States Patent
Amiche et al.

(10) Patent No.: US 6,187,292 B1
(45) Date of Patent: Feb. 13, 2001

(54) SILICA CAPABLE OF BEING USED IN TOOTHPASTE COMPOSITIONS

(75) Inventors: Frédéric Amiche, Aulnay-Sous-Bois; Adrien Dromard, Lyons, both of (FR)

(73) Assignee: Rhodia Chimie, Courbevoie Cedex (FR)

(*) Notice: Under 35 U.S.C. 154(b), the term of this patent shall be extended for 0 days.

(21) Appl. No.: 09/194,341

(22) PCT Filed: Jun. 4, 1997

(86) PCT No.: PCT/FR97/00987

§ 371 Date: Feb. 19, 1999

§ 102(e) Date: Feb. 19, 1999

(87) PCT Pub. No.: WO97/46485

PCT Pub. Date: Dec. 11, 1997

(30) Foreign Application Priority Data

Jun. 6, 1996 (FR) .................................................. 96 07187

(51) Int. Cl.⁷ .............................. A61K 7/16; C01B 33/12
(52) U.S. Cl. ........................ 424/49; 423/335; 423/339; 51/308
(58) Field of Search .................. 423/335, 339; 424/49; 51/308

(56) References Cited

U.S. PATENT DOCUMENTS

| | | | |
|---|---|---|---|
| 5,225,177 | * 7/1993 | Wason et al. | 423/334 |
| 5,279,815 | * 1/1994 | Wason et al. | 424/52 |
| 5,403,570 | * 4/1995 | Chevallier et al. | 423/339 |
| 5,512,271 | * 4/1996 | McKeown et al. | 424/49 |
| 5,587,416 | * 12/1996 | Chevallier et al. | 524/492 |
| 5,603,920 | * 2/1997 | Rice | 424/49 |
| 5,869,028 | * 2/1999 | McGill et al. | 424/49 |
| 5,932,191 | * 8/1999 | Chevallier et al | 424/52 |
| 5,964,937 | * 10/1999 | Stanier | 106/492 |
| 6,001,322 | * 12/1999 | Chevallier et al. | 423/339 |

FOREIGN PATENT DOCUMENTS

| | | |
|---|---|---|
| 0 064 620 | 11/1982 | (EP) . |
| 1 054 175 | 2/1954 | (FR) . |
| 2 090 963 | 1/1972 | (FR) . |
| 95 18066 | 7/1995 | (WO) . |

\* cited by examiner

*Primary Examiner*—Shep K. Rose
(74) *Attorney, Agent, or Firm*—Burns, Doane, Swecker & Mathis, L.L.P.

(57) ABSTRACT

The invention discloses an abrasive precipitation silica useable in toothpaste compositions, said silica having a BET specific surface ranging from 15 to 300 $m^2/g$, a DOP oil absorption ranging from 40 to 160 ml/g, a median particle diameter of at least 10 $\mu m$, generally ranging from 12 to 30 $\mu m$, a particle cohesion factor of at least 85% about for a median particle diameter ranging from 12 to 20 $\mu m$. Method for preparing silica by reacting an alkaline metal silicate with an acidifying agent, to form a silica slurry, separating and optionally drying the recuperated silica suspension, the operation for forming the slurry being effected according to the following steps: a first step consisting in using one initial heel solution constituted of water, an electrolyte salt of the alkaline or alkaline-earth metal group and optionally of one acidobasic agent; a second step consisting in introducing the silicate and the acidifying agent, the reaction medium pH remaining constant from 4 to 7 and particularly from 5.8 to 6.7; and a third optional step, consisting in acidifying the reaction medium until a silica slurry with a pH of less than 6 and particularly of 4 is obtained. The silica is useful in toothpaste compositions. Toothpaste compositions containing the said silica are also disclosed.

20 Claims, No Drawings

SILICA CAPABLE OF BEING USED IN TOOTHPASTE COMPOSITIONS

The present invention relates to an abrasive precipitation silica with a median diameter of at least 10 μm and with good grain cohesion, which can be used in toothpaste compositions, in particular in anti-tartar compositions, and to a process for preparing the said silica; the invention also relates to toothpaste compositions containing the said silica.

The abrasive agents (in particular silica) used in toothpaste compositions generally have a median particle diameter of less than or equal to 10 μm, less than 1.5% of the weight of the said particles having a diameter of greater than 44 μm.

Certain formulations, in particular those with an anti-tartar effect, can require the use of larger-sized abrasive agents.

A so-called "crunchy" effect, i.e. a granular sensation in the mouth, and throughout brushing, may be desired by the consumer. An abrasive can achieve this effect only if it has a sufficient grain cohesion during brushing.

This problem can be solved by silica gels (continuous three-dimensional rigid structure) with a BET specific surface generally of greater than 300 m²/g. However, the process for preparing these gels requires long and expensive washing and filtration steps.

Precipitation silicas (aggregates consisting of discrete particulate entities bound together by weak bonds) are obtained by processes which are simpler to carry out, but do not have a sufficient level of grain cohesion for the desired application.

The Applicant has found an abrasive silica with a median diameter of at least 10 μm and with sufficient grain cohesion, which can be obtained by a simple process, such as a process for the preparation of silica by precipitation.

A first subject of the invention consists of an abrasive precipitation silica which can be used in toothpaste compositions, this silica having
- a BET specific surface of about 15 to 300 m²/g, preferably of about 20 to 250 m²/g
- a DOP oil uptake of about 40 to 160 ml/g, preferably of about 50 to 140 ml/g
- a median particle diameter of at least 10 μm, generally of about 12 to 30 μm
- a particle cohesion factor of at least 85% approximately for a median particle diameter of about 12 μm to 20 μm.

The said silica also has a CTAB specific surface of about 10 to 120 m²/g, preferably of about 15 to 100 m²/g.

The BET specific surface is measured according to the Brunauer—Emmet—Teller method described in "The Journal of the American Chemical Society", Vol. 60, page 309, February 1938 and corresponding to ISO standard 5794/1 (Annex D).

The DOP oil uptake is determined according to ISO standard 787/5 using dioctyl phthalate.

The silica particle cohesion is quantified using a specific test of cohesion by ultrasound; this test allows the change in the median diameter $d_{50}$ of a silica suspension to be evaluated by measuring the particle size before and after the ultrasound treatment.

According to this test, the particle size measurement (by laser scattering using a Laser Sympatec granulometer) is carried out on a silica suspension treated with ultrasound using a Vibracell Bioblock sonicator (600 W power rating), equipped with a probe 19 mm in diameter, a timer and a converter, according to the following operation:

Preparation of the Silica Suspention

A homogeneous suspension of 15 g of silica in 135 g of water is prepared using a Rayneri impeller-disperser; 70 g of suspension are then transferred into a 50 ml glass flask.

Ultrasound Treatment

The probe, which has been preadjusted, is introduced into the flask to a depth of 4 cm, without contact with the glass walls; the timer is programmed with pulsation over a period of 2000 seconds, so as to obtain an active ultrasound cycle of 600 seconds.

The ultrasound cycle is started after the flask is sealed.

Checking the Particle Size

After manual homogenization of the sealed flask, about 2 ml of homogeneous suspension are removed with a pipette, and this suspension is then poured into the granulometer cuvette, after adjusting the level of water, if necessary, in order to obtain an optical concentration of 20%±3%.

After ultrasound dispersion of the suspension in the cuvette for 30 s, the median diameter $d_{50}$ is measured using a 100 mm focal device.

The cohesion factor of the test silica is then calculated; the higher the cohesion of the silica, the higher this factor.

Cohesion Factor

The initial median particle diameter $d_{50i}$ is measured on the homogeneous silica suspension before the ultrasound treatment.

The final median diameter $d_{50f}$ is measured on the homogeneous silica suspension after the ultrasound treatment.

The cohesion factor CF, as a (%) is calculated according to the following equation:

$$CF = (d_{50f}/d_{50i}) \times 100$$

A CF value of 100 corresponds to the maximum cohesion value.

The CTAB specific surface is the external surface area determined according to the standard NFT 45007 (November 1987).

A second subject of the invention consists of a process for preparing abrasive silica with good grain cohesion, which can be used in toothpaste compositions, by reacting an alkali metal M silicate, with an $SiO_2/M_2O$ ratio of about 2 to 4, preferably of about 3 to 3.8, with an acidifying agent, optional maturation of the silica mash formed, separation and optional drying of the silica suspension recovered and optional grinding, the said process being characterized in that the operation for forming the silica mash is carried out according to the following steps:

a first step consisting in using an initial stock solution consisting of water, an electrolytic salt from the group of alkali metals or alkaline-earth metals and optionally an acidobasic agent, at a temperature of about 70 to 98° C., preferably of about 80 to 95° C., the amount of electrolyte present being about 0.1 to 1 mol of alkali-metal electrolytic salt or of about 10 to 100 mmol of alkaline-earth-metal electrolytic salt per liter of stock solution;

a second step consisting in introducing into the said stock solution the alkali metal silicate as an aqueous solution and the acidifying agent, under conditions such that the pH of the reaction medium remains more or less constant and at a value of about 4 to 7, preferably of about 5.5 to 7, and particularly of about 5.8 to 6.7, the said reagents being introduced until the desired silica concentration is obtained in the said medium, the reaction medium being maintained at a temperature of about 70 to 98° C., preferably of about 80 to 95° C.;

and, after optional maturation, a third optional step consisting in acidifying the reaction medium until a silica mash with a pH of less than 6, preferably less than 5, most particularly of about 4, is obtained.

The choice of the silicate and of the acidifying agent to carry out the process of the invention is made in a manner which is well known per se.

The alkali metal silicate is advantageously a sodium or potassium silicate. sodium silicates may be mentioned most particularly.

The said silicate is used in the form of an aqueous solution with a concentration, expressed as $SiO_2$, of about 150 to 400 g/l, preferably of about 200 to 400 g/l.

The acidifying agent generally used is a strong inorganic acid such as sulphuric acid, nitric acid or hydrochloric acid, or an organic acid such as acetic acid, formic acid or carbonic acid. Preferably, it is sulphuric acid. This acid can be used in dilute or concentrated form, preferably in the form of an aqueous solution with a concentration of about 60 to 400 g/l.

Among the electrolytes mention may be made in particular of the metal salt of the starting silicate and of the acidifying agent, i.e. preferably sodium sulphate.

An acidobasic agent can be used in the initial stock solution to ensure that the pH of the said stock solution is close to that chosen for the second step of the process, it being possible for this pH to be adjusted using a strong acid or a strong base. Acidobasic agents which may be mentioned in particular are alkali metal hydrogen phosphates.

The said stock solution can also contain silicates; however, the amount of optional silicate ions, expressed as $SiO_2$, is less than 10 grams per liter of stock solution. Preferably, the stock solution contains no silicate ions.

The stock solution obtained is brought to a temperature of about 70 to 98° C., preferably of about 80 to 95° C., and is kept stirring.

The second step consists in adding the silicate solution and the acidifying agent simultaneously to the stock solution maintained under vigorous stirring.

The respective amounts of alkali metal silicate and of acidifying agent are chosen so as to keep the pH of the reaction medium at a more or less constant value of about 4 to 7, preferably of about 5.5 to 7, most particularly of about 5.8 to 6.7, throughout the introduction of the two reagents.

These two solutions are introduced while keeping the medium at a temperature of about 70 to 98° C., preferably of about 80 to 95° C.

The introduction of the silicate solution is stopped when the desired amount of silica formed is obtained. This amount is at least 65 grams per liter approximately, generally about 65 to 120 grams per liter, preferably about 70 to 100 grams per liter of reaction medium.

The optional third step is carried out by adding the acidifying agent to the reaction medium with stirring, under the same temperature conditions, until a pH of less than 6, preferably less than 5 and most particularly of about 4, is obtained, so as to improve the filtration and washing operations.

According to one embodiment, the medium obtained at the end of the second step, after stopping the introduction of the silicate solution, is left to mature under the same temperature conditions, for at least about ten minutes, preferably from 10 minutes to 2 hours, before reintroducing the acidifying agent in order to carry out the optional third step.

At the end of the third step, after stopping the addition of the acidifying agent, the reaction medium is optionally left to mature, under the same temperature conditions. This optional maturation operation can last from about 10 minutes to 2 hours.

After the operations described above, a silica mash is obtained, which is then separated (liquid-solid separation); this operation generally consists of a filtration (for example using a rotary filter under vacuum), followed by washing with water.

The silica suspension thus recovered (filter cake) contains at least 35% approximately by mass of solids. It is then optionally dried, for example using a convection dryer (sprayer, spin-flash, tunnel oven, etc.) or a conduction dryer (rotating oven, screw dryer, scaler, drum dryer, etc.).

The silica in suspension or in dry form has a particle cohesion factor of at least 85% approximately, for a median particle diameter of about 12 $\mu$m to 20 $\mu$m.

This silica can optionally be ground until the desired median particle diameter $d_{50}$ is obtained, generally of about 10 to 40 $\mu$m, preferably of about 12 to 30 $\mu$m.

The silica with good grain cohesion, which forms the subject of the invention or which is obtained according to the process which forms the subject of the invention, is particularly suitable for use as an abrasive agent in toothpaste compositions.

When the silica is in the form of a suspension, this suspension can be stabilized by any known means, in particular using a hydrocolloid, in particular using a polysaccharide such as xanthan gum, guar gum, water-soluble cellulose ethers, etc.

A subject of the present invention is also the use of the silica which forms the subject of the invention or which is obtained according to the process of the invention as an abrasive agent in toothpaste compositions, as well as toothpaste compositions comprising the said silica. The said silica can be present in the said toothpaste compositions in a proportion of about 5 to 50% by weight of the said compositions.

These compositions can also contain other common ingredients, in particular other inorganic, water-insoluble abrasive agents, thickeners, wetting agents, etc.

As other abrasive agents, mention may be made in particular of abrasive silicas with a standard particle size (less than 10 $\mu$m), calcium carbonates, hydrated alumina, bentonite, aluminium silicate, zirconium silicate, and sodium, potassium, calcium and magnesium metaphosphates and phosphates. The total amount of abrasive powder (s) can constitute about 5 to 50% of the weight of the dental composition.

Among the thickeners, mention may be made most particularly of thickening silicas in an amount of about 1 to 15% of the weight, xanthan gum, guar gum, carrageenans, cellulose derivatives and alginates, in an amount which can range up to 5% of the weight of the said composition, etc.

Among the wetting agents, mention may be made, for example, of glycerol, sorbitol, polyethylene glycols, polypropylene glycols and xylitol, in an amount of about 2 to 85%, preferably of about 3 to 55%, of the weight of toothpaste composition expressed as solids.

These toothpaste compositions can also contain surfactants, detergents, dyes, antibacterial agents, fluoro derivatives, opacifiers, flavourings, sweeteners, anti-tartar agents, anti-plaque agents, bleaching agents, sodium bicarbonate, antiseptics, enzymes, natural extracts (camomile, thyme, etc.), etc.

The examples which follow are given for illustrative purposes.

COMPARATIVE EXAMPLE 1

The following are introduced into a 25 liter reactor:

1110 g of an aqueous sodium silicate solution with an $SiO_2/Na_2O$ ratio of 3.4, containing 236 g/l of $SiO_2$ 1.8 liters of water 58.6 g of sodium sulphate.

The temperature is brought to 90° C. with vigorous stirring.

856 g of sulphuric acid at 80 g/l are then added in order to bring the pH to 9.2.

An aqueous sodium silicate solution with an $SiO_2/Na_2O$ ratio of 3.4, containing 236 g/l of $SiO_2$, and an aqueous sulphuric acid solution at 80 g/l are then introduced simultaneously, at a constant pH of 9.2, so as to reach a concentration of 76 g of $SiO_2$ per liter of suspension.

The addition of acid is continued until a pH of 4 is obtained.

The product is then filtered off, washed and dried by spraying.

COMPARATIVE EXAMPLE 2

3 liters of water are introduced into a 25 liter reactor.

The temperature is brought to 80° C. with vigorous stirring.

An aqueous sodium silicate solution with an $SiO_2/Na_2O$ ratio of 3.5, containing 230 g/l of $SiO_2$, and an aqueous sulphuric acid solution at 80 g/l are added simultaneously, over 80 minutes and at a constant pH of 6, so as to reach a concentration of 84 g of $SiO_2$ per liter of suspension.

The addition of acid is continued until a pH of 4 is obtained.

The product is then filtered off, washed and dried by spraying.

EXAMPLE 3

3 liters of water and 156 g of sodium sulphate are introduced into a 25 liter reactor.

The temperature is brought to 80° C. with vigorous stirring.

An aqueous sodium silicate solution with an $SiO_2/Na_2O$ ratio of 3.5, containing 230 g/l of $SiO_2$, and an aqueous sulphuric acid solution at 80 g/l are added simultaneously, over 80 minutes and at a constant pH of 6, so as to reach a concentration of 84 g of $SiO_2$ per liter of suspension.

The addition of acid is continued until a pH of 4 is obtained.

The product is then filtered off, washed and dried by spraying.

EXAMPLE 4

3 liters of water and 156 g of sodium sulphate are introduced into a 25 liter reactor.

The temperature is brought to 70° C. with vigorous stirring.

An aqueous sodium silicate solution with an $SiO_2/Na_2O$ ratio of 3.5, containing 230 g/l of $SiO_2$, and an aqueous sulphuric acid solution at 80 g/l are added simultaneously, over 80 minutes and at a constant pH of 6, so as to reach a concentration of 84 g of $SiO_2$ per liter of suspension.

The addition of acid is continued until a pH of 4 is obtained.

The product is then filtered off, washed and dried by spraying.

EXAMPLE 5

3 liters of water and 156 g of sodium sulphate are introduced into a 25 liter reactor.

The temperature is brought to 90° C. with vigorous stirring.

An aqueous sodium silicate solution with an $SiO_2/Na_2O$ ratio of 3.5, containing 230 g/l of $SiO_2$, and an aqueous sulphuric acid solution at 80 g/l are added simultaneously, over 80 minutes and at a constant pH of 6, so as to reach a concentration of 84 g of $SiO_2$ per liter of suspension.

The addition of acid is continued until a pH of 4 is obtained.

The product is then filtered off, washed and dried by spraying.

EXAMPLE 6

3 liters of water and 156 g of sodium sulphate are introduced into a 25 liter reactor.

The temperature is brought to 85° C. with vigorous stirring.

An aqueous sodium silicate solution with an $SiO_2/Na_2O$ ratio of 3.5, containing 230 g/l of $SiO_2$, and an aqueous sulphuric acid solution at 80 g/l are added simultaneously, over 80 minutes and at a constant pH of 6, so as to reach a concentration of 84 g of $SiO_2$ per liter of suspension.

The addition of acid is continued until a pH of 4 is obtained.

The product is then filtered off, washed and dried by spraying.

EXAMPLE 7 AND 8

3 liters of water, 96 g of sodium sulphate and 24 g of sodium monohydrogen phosphate are introduced into a 25 liter reactor. The pH of the medium is 8.5.

The temperature is; brought to 85° C. with vigorous stirring.

The pH of the medium is brought to 6.2 by addition of sulphuric acid.

An aqueous sodium silicate solution with an $SiO_2/Na_2O$ ratio of 3.5, containing 230 g/l of $SiO_2$, and an aqueous sulphuric acid solution at 80 g/l are added simultaneously, over 80 minutes and at a constant pH of 6.2, so as to reach a concentration of 84 g of $SiO_2$ per liter of suspension.

The addition of acid is continued until a pH of 4 is obtained.

The product is then filtered off and washed.

A suspension containing 49% solids is obtained (Example 7).

This suspension is then dried by spraying (Example 8).

The characteristics of the silicas obtained in Examples 1 to 8 are given in Table 1 below.

| Example | BET ($m^2/g$) | CTAB ($m^2/g$) | DOP uptake ml/g | $d_{50i}$ $\mu m$ | $d_{50f}$ $\mu m$ | CF % |
|---|---|---|---|---|---|---|
| 1 | 40 | 25 | 70 | 14.7 | 11.2 | 76 |
| 2 | 222 | — | 87 | 14.5 | 11.8 | 81 |
| 3 | 80 | 51 | 80 | 15.1 | 14.3 | 95 |
| 4 | 250 | 89 | 132 | 16.3 | 14.8 | 90 |
| 5 | 40 | 26 | 70 | 15.4 | 15.4 | 100 |
| 6 | 60 | 39 | 81 | 17.2 | 16 | 93 |
| 7 (suspension) | — | — | — | 14.9 | 13.26 | 89 |
| 8 | 71 | 44 | 76 | 14.6 | 13 | 89 |

It is observed that the products prepared according to the process of the invention, with a $d_{50i}$ value of about 15 μm, have a cohesion factor CF of at least 85%.

EXAMPLE 9

The silica obtained in any one of Examples 3 to 6 or 8 is used to obtain the following toothpaste composition.

| | | |
|---|---|---|
| Sorbitol (50% solution) | | 47% |
| Silica of Examples 3 to 6 or 8 | | 19% |
| Thickening silica | | 3% |
| Tetrasodium pyrophosphate | | 1% |
| Tetrapotassium pyrophosphate | | 4% |
| Titanium dioxide | | 0.5% |
| Xanthan gum | | 0.8% |
| Sodium saccharinate | | 0.2% |
| Sodium benzoate | | 0.3% |
| Sodium fluoride | | 0.22% |
| Sodium lauryl sulphate | | 1.4% |
| Flavouring | | 1% |
| Deionized water | qs | 100% |

What is claimed is:

1. Abrasive precipitation silica with
   a BET specific surface of about 15 to 300 m$^2$/g,
   a DOP oil uptake of about 40 to 160 ml/g, generally of about 12 to 30 μm
   a particle cohesion factor of at least 85% approximately for a median particle diameter of about 12 μm to 20 μm.

2. Silica according to claim 1, having a CTAB specific surface of about 10 to 120 m$^2$/g.

3. Process for preparing silica by reacting an alkali metal M silicate, with an SiO$_2$/M$_2$O ratio of about 2 to 4, with an acidifying agent, optional maturation of the silica mash formed, separation and optional drying of the silica suspension recovered and optional grinding, wherein the operation for forming the silica mash is carried out according to the following steps:
   a first step comprises using an initial stock solution of water, an electrolytic salt from the group of: alkali metals, alkaline-earth metals, and an alkali metal M silicate; and optionally an acidobasic agent, at a temperature of about 70 to 98° C., the amount of electrolyte present being about 0.1 to 1 mol of alkali-metal electrolytic salt or of about 10 to 100 mmol of alkaline-earth-metal electrolytic salt per liter of stock solution or less than 10 g/l of alkali metal silicate, expressed as SiO$_2$;
   a second step comprising introducing into said stock solution the alkali metal silicate as an aqueous solution and the acidifying agent, under conditions such that the pH of the reaction medium remains more or less constant and at a value of about 5.5 to less than 7, said reagents being introduced until the desired silica concentration is obtained in said medium, the reaction medium being maintained at a temperature of about 70 to 98° C.;
   and, after optional maturation, a third optional step comprising acidifying the reaction medium until a silica mash with a pH of less than 6 is obtained.

4. Process according to claim 3, wherein the alkali metal silicate is a sodium or potassium silicate.

5. Process according to claim 3 wherein the alkali metal silicate is a sodium silicate used in the form of an aqueous solution with a concentration, expressed as SiO$_2$, of about 150 to 400 g/l.

6. Process according to claim 3, wherein the acidifying agent is an inorganic or organic acid.

7. Process according to claim 6, wherein the acidifying agent is sulphuric acid, nitric acid, hydrochloric acid, acetic acid, formic acid or carbonic acid.

8. Process according to claim 7, wherein the acidifying agent is sulphuric acid, which is used in the form of an aqueous solution with a concentration of about 60 to 400 g/l.

9. Process according to claim 3, wherein the electrolyte is a metal salt of the starting silicate and of the acidifying agent.

10. Process according to claim 3, wherein the acidobasic agent is an alkali metal hydrogen phosphate.

11. Process according to claim 3 wherein the second step comprising adding the silicate solution and the acidifying agent simultaneously to the stock solution while stirring, the addition being in respective amounts of alkali metal silicate and of acidifying agent which are chosen so as to keep the pH of the reaction medium at a more or less constant value of about 5.5 to less than 7, throughout the introduction of the two reagents.

12. Process according to claim 3, wherein the third step is carried out by adding the acidifying agent to the reaction medium with stirring, until a pH of less than 6, is obtained.

13. Process according to claim 3, wherein the medium obtained at the end of the second step, after stopping the introduction of the silicate solution, is left to mature for at least about ten minutes.

14. Process according to claim 3, wherein at the end of the third step, after stopping the addition of the acidifying agent, the reaction medium is left to mature for about 10 minutes to 2 hours.

15. Process according to claim 3, wherein the operation for formation of the silica mash is carried out at a temperature of about 70 to 98° C.

16. Toothpaste compositions comprising about 5 to 50% of their weight of silica according to claim 1 and an acceptable carrier therefor.

17. Toothpaste composition according to claim 16, comprising at least one common ingredient comprising other abrasive agents, thickeners, wetting agents, surfactants, detergents, dyes, antibacterial agents, fluoro derivatives, opacifiers, flavourings, sweeteners, anti-tartar agents, anti-plaque agents, bleaching agents, sodium bicarbonate, antiseptics, enzymes or natural extracts.

18. The silica according to claim 1, having a BET specific surface area of about 20 to 250 m$^2$/g, a DOP oil uptake of about 50 to 140 ml/g and a median particle diameter of about 12 to 30 μm.

19. A method for cleaning teeth, said method comprising an effective amount of the abrasive precipitation silica according to claim 1 to a patient in need of such cleaning.

20. The process according to claim 3, wherein the pH of the reaction medium in the second step remains more or less constant and at a value of 5.5–6.7.

* * * * *